(12) United States Patent
Kim et al.

(10) Patent No.: US 10,456,097 B2
(45) Date of Patent: Oct. 29, 2019

(54) X-RAY GENERATION APPARATUS FOR INTRA-ORAL X-RAY IMAGING, GUIDE HOLDER, AND INTRA-ORAL X-RAY IMAGING SYSTEM COMPRISING SAME

(71) Applicants: VATECH Co., Ltd., Gyeonggi-do (KR); VATECH EWOO Holdings Co., Ltd., Gyeonggi-do (KR)

(72) Inventors: Yeong Kyun Kim, Gyeonggi-do (KR); Tae Woo Kim, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 244 days.

(21) Appl. No.: 15/521,391

(22) PCT Filed: Oct. 26, 2015

(86) PCT No.: PCT/KR2015/011331
§ 371 (c)(1),
(2) Date: Apr. 24, 2017

(87) PCT Pub. No.: WO2016/064257
PCT Pub. Date: Apr. 28, 2016

(65) Prior Publication Data
US 2017/0311911 A1    Nov. 2, 2017

(30) Foreign Application Priority Data

Oct. 24, 2014  (KR) ........................ 10-2014-0145294
Jan. 30, 2015  (KR) ........................ 10-2015-0015484

(51) Int. Cl.
*A61B 6/14*  (2006.01)
*A61B 5/00*  (2006.01)
(Continued)

(52) U.S. Cl.
CPC ................ *A61B 6/145* (2013.01); *A61B 5/00* (2013.01); *A61B 6/025* (2013.01); *A61B 6/032* (2013.01);
(Continued)

(58) Field of Classification Search
CPC ........... A61B 6/145; A61B 5/00; A61B 6/025; A61B 6/032; A61B 6/14; A61B 6/4007;
(Continued)

(56) References Cited

U.S. PATENT DOCUMENTS 6,018,562 A    1/2000   Willson
2005/0226364 A1   10/2005   Bernard De Man et al.
(Continued)

FOREIGN PATENT DOCUMENTS

JP    2005-288152 A   10/2005
JP    2012-501212 A    1/2012
(Continued)

OTHER PUBLICATIONS

European Patent Office, European Search Report of corresponding EP Patent Application No. 15853610.2, dated Aug. 14, 2018.

*Primary Examiner* — Courtney D Thomas
(74) *Attorney, Agent, or Firm* — IP Legal Services, LLC

(57) ABSTRACT

Disclosed is an X-ray generation apparatus for intra-oral X-ray imaging, a guide holder, and an X-ray imaging system comprising the same. The X-ray generation apparatus includes a body and a plurality of X-ray sources disposed in different positions of the body, and configured to irradiate X-rays to a field of view, wherein the body moves along a predetermined trajectory for the field of view.

11 Claims, 10 Drawing Sheets

(51) Int. Cl.
  *A61B 6/02* (2006.01)
  *A61B 6/03* (2006.01)
  *A61B 6/00* (2006.01)
  *H01J 35/06* (2006.01)
(52) U.S. Cl.
  CPC .............. *A61B 6/14* (2013.01); *A61B 6/4007* (2013.01); *A61B 6/4411* (2013.01); *A61B 6/461* (2013.01); *A61B 6/52* (2013.01); *H01J 35/065* (2013.01); *A61B 6/54* (2013.01)
(58) Field of Classification Search
  CPC ......... A61B 6/4411; A61B 6/461; A61B 6/52; A61B 6/54; H01J 35/065
  USPC ................................................ 378/38–40, 92
  See application file for complete search history.

(56) References Cited

U.S. PATENT DOCUMENTS

| | | |
|---|---|---|
| 2009/0185660 A1 | 7/2009 | Zou et al. |
| 2013/0294666 A1 | 11/2013 | Bultema |
| 2014/0111535 A1 | 4/2014 | Cocco et al. |
| 2014/0185750 A1 | 7/2014 | Sung et al. |
| 2016/0317107 A1* | 11/2016 | Zhou ..................... A61B 6/547 |

FOREIGN PATENT DOCUMENTS

| | | |
|---|---|---|
| KR | 10-2014-0049919 A | 4/2014 |
| KR | 10-2014-0087213 A | 7/2014 |
| WO | 97/18462 A1 | 5/1997 |

* cited by examiner (a)

(b)

X-RAY GENERATION APPARATUS FOR INTRA-ORAL X-RAY IMAGING, GUIDE HOLDER, AND INTRA-ORAL X-RAY IMAGING SYSTEM COMPRISING SAME

CROSS REFERENCE TO RELATED APPLICATIONS

This application is a National Stage Patent Application of PCT International Patent Application No. PCT/KR2015/011331 (filed on Oct. 26, 2015) under 35 U.S.C. § 371, which claims priority to Korean Patent Application Nos. 10-2014-0145294 (filed on Oct. 24, 2014) and 10-2015-0015484 (filed on Jan. 30, 2015), the teachings of which are incorporated herein in their entireties by reference.

TECHNICAL FIELD

The present invention relates generally to an intra-oral X-ray radiography. More particularly, the present invention relates to an X-ray generation apparatus for intra-oral X-ray imaging and an intra-oral X-ray imaging system including the same, in which various types of images of a tooth and surrounding tissue, namely a field of view, can be obtained.

BACKGROUND ART

As is well known, X-rays are attenuated according to an X-ray attenuation coefficient, such as photoelectric effect, Compton scattering, and the like, of a substance placed in a path of the X-rays.

X-ray radiography is a radiography method using straightness and attenuation of X-rays, and based on the amount of attenuation accumulated in the course of the X-rays passing through a field of view, it provides an X-ray image of the internal structure of the field of view. To achieve this, an X-ray imaging system includes: an X-ray generation apparatus configured to irradiate X-rays to a field of view; an X-ray sensor disposed to face the X-ray generation apparatus with the field of view therebetween, and configured to detect X-rays that have penetrated through the field of view; and an image processing apparatus configured to construct a gray-level X-ray image of an internal structure of the field of view by using X-ray projection data, as a detection result detected by the X-ray sensor.

Meanwhile, in recent years, X-ray radiography has been rapidly evolving into DR (Digital Radiography) using digital sensors due to the development of semiconductor and information processing technologies, whereby image processing technology has also been developed and is used in various ways according to the purpose and application field.

As an example, FIG. 1 is a view showing principle of intra-oral X-ray radiography mainly used in the dental field, and an intra-oral X-ray image according to the intra-oral X-ray radiography.

As shown in the drawing, intra-oral X-ray radiography is an X-ray radiography technology for obtaining an X-ray image of a limited field of view of a subject, and is performed as follows: an X-ray sensor S is placed inside the subject's mouth; and X-rays are irradiated from an X-ray generation apparatus outside the mouth to the X-ray sensor S, thereby obtaining an X-ray image of a tooth and surrounding tissue that is disposed between the X-ray generation apparatus and the X-ray sensor S. The intra-oral X-ray image has advantages of low distortion, excellent resolution and sharpness, and relatively low radiation exposure, so it is mainly used for implant treatment or endodontic treatment requiring high resolution.

However, the conventional intra-oral X-ray image is a two-dimensional transmission image, in which results of X-ray attenuation by all the substances including a tooth and surrounding tissue, namely a field of view, that exist between the X-ray generation apparatus and the X-ray sensor S are superimposed on a two-dimensional plane defined as the incident surface of the X-ray sensor S. Thus, with the intra-oral X-ray image alone, it is impossible to identify a depth of a desired portion, such as s focus, within the area of the X-ray image, that is, relative positional relationship of the path of the X-rays.

Accordingly, for more accurate diagnosis, such as a three-dimensional location of a desired portion of the intra-oral X-ray image, CT scans are additionally performed to obtain a three-dimensional X-ray image of the field of view or diagnosis is made based entirely on the empirical knowledge of the radiologist. However, in the former case, the overall length of time and procedures are complicated and subject fatigue is increased, as well as a serious problem of unnecessarily increasing radiation exposure, and in the latter case, there is a deviation of diagnostic results according to the personal experience of the radiologist, and there is a high possibility of subjective judgment, which lowers the reliability of diagnosis.

DISCLOSURE

Technical Problem

Accordingly, the present invention has been made keeping in mind the above problems occurring in the related art, and an object of the present invention is to provide a specific method of not only providing a two-dimensional transmission image (hereinafter, referred to as 'transmission image') but also a three-dimensional tomosynthesis image (hereinafter, referred to as 'tomosynthesis image') and a three-dimensional CT (Computed Tomography) image (hereinafter, referred to as 'CT image') of a tooth and surrounding tissue inside a subject's mouth, namely a field of view by acquiring three-dimensional location information on an arbitrary point within the field of view, particularly, depth information about the direction of X-rays based on the result of intra-oral X-ray radiography.

To achieve this, a specific object of the present invention is to provide an X-ray generation apparatus for intra-oral X-ray imaging and an intra-oral X-ray imaging system including the same, which are capable of providing a transmission image, a tomosynthesis image, and a CT image of a tooth and surrounding tissue inside a mouth.

Technical Solution

In order to achieve the above object, according to some aspect of the present invention, there is provided an X-ray generation apparatus for intra-oral X-ray imaging, which irradiates X-rays to a field of view inside a mouth from outside the mouth, the X-ray generation apparatus including: a single body; and a plurality of X-ray sources disposed in different positions of the body, and configured to irradiate X-rays to the field of view at a same angle or different angles.

Each of the plurality of X-ray sources may irradiate X-rays to form a unit frame of X-ray image for the field of view.

The X-ray generation apparatus may further include a controller provided in the body, and configured to supply power and control signals for driving the plurality of X-ray sources. Here, the body may move along a predetermined trajectory for the field of view, and the controller may drive the plurality of X-ray sources in conjunction with the movement of the body.

The plurality of X-ray sources may move with respect to the body along a predetermined trajectory for the field of view, and the controller may drive the plurality of X-ray sources in conjunction with movement of the plurality of X-ray sources.

Each of the X-ray sources may include an X-ray source module adopting an electric field emission type nanostructure emitter, and the X-ray source module may be detachably coupled to the body.

The plurality of X-ray sources may be arranged on the body, and includes a plurality of X-ray source elements adopting an electric field emission type nanostructure emitter, wherein each of the X-ray sources includes at least one X-ray source element.

The plurality of X-ray sources may irradiate the X-rays at a rate of 1 to 20 frames per second.

In order to achieve the above object, according to some aspect of the present invention, there is provided an intra-oral X-ray imaging system, which irradiates X-rays to a field of view inside a mouth from outside the mouth, the intra-oral X-ray imaging system including: an X-ray generation apparatus including a body and a plurality of x-ray sources disposed in different positions of the body, and configured to irradiate X-rays to form a one-frame X-ray image of the field of view; an X-ray sensor apparatus disposed inside the mouth to face the X-ray generation apparatus with the field of view therebetween, and configured to detect the X-rays irradiated from the X-ray generation apparatus, on a frame-by-frame basis; and an image processing apparatus configured to produce and display at least one X-ray image of a two-dimensional transmission image, a tomosynthesis image, and a three-dimensional CT image of the field of view, based on a detection result on the frame-by-frame basis of the X-ray sensor apparatus.

The X-ray sensor apparatus may include a curved X-ray sensor.

The X-ray generation apparatus may irradiate the X-rays at a rate of 1 to 20 frames per second, and the X-ray sensor apparatus may detect the X-rays at a rate of 1 to 20 frames per second.

The image processing apparatus may display the X-ray image as a video clip.

The X-ray sensor apparatus may include: an X-ray sensor configured to detect the X-rays; and a readout circuit configured to read out a detection result of the X-ray sensor on a multi-channel basis for each frame.

The X-ray sensor apparatus may include two or more X-ray sensors disposed along a back and forth direction with respect to the X-ray generation apparatus.

In order to achieve the above object, according to some aspect of the present invention, there is provided a guide holder including: at least two source fasteners disposed outside a subject's mouth, and configured to allow at least two X-ray sources respectively irradiating X-rays to be fastened one-to-one thereto; a sensor fastener disposed inside the subject's mouth, and configured to fasten an X-ray sensor apparatus that detects the X-rays irradiated from the respective X-ray sources; and a loader configured to connect the source fasteners and the sensor fastener.

The sensor fastener may be configured to allow two or more X-ray sensor apparatuses disposed in a back and forth direction with respect to the source fastener to be fastened thereto.

Advantageous Effects

An X-ray generation apparatus for intra-oral X-ray imaging according to the present invention and an intra-oral X-ray imaging system including the same are capable of providing not only a two-dimensional transmission image but also a three-dimensional tomosynthesis image and a three-dimensional CT image of a tooth and surrounding tissue inside a subject's mouth, namely a field of view. Accordingly, it is possible to identify three-dimensional location information on an arbitrary point within the field of view, particularly, depth information about the direction of X-rays based on the result of intra-oral X-ray radiography without performing additional X-ray radiography, such as computed tomography.

Further, according to the present invention, without large-sized equipment that includes an X-ray generation apparatus and an X-ray detector rotating around the subject's head, it is possible to obtain various types of X-ray radiography images including a CT image of a part that needs medical treatment. Meanwhile, by using a small-sized intraoral x-ray sensor that is disposed inside the mouth, it is possible dramatically reduce X-ray exposure to the subject compared to the high-quality imaging result. Thereby, diagnostic accuracy can be greatly improved without significant burden on X-ray exposure in the dental field.

MODE FOR INVENTION

Hereinbelow, preferred embodiments of the present invention will be described in detail with reference to the accompanying drawings.

Figure 1:
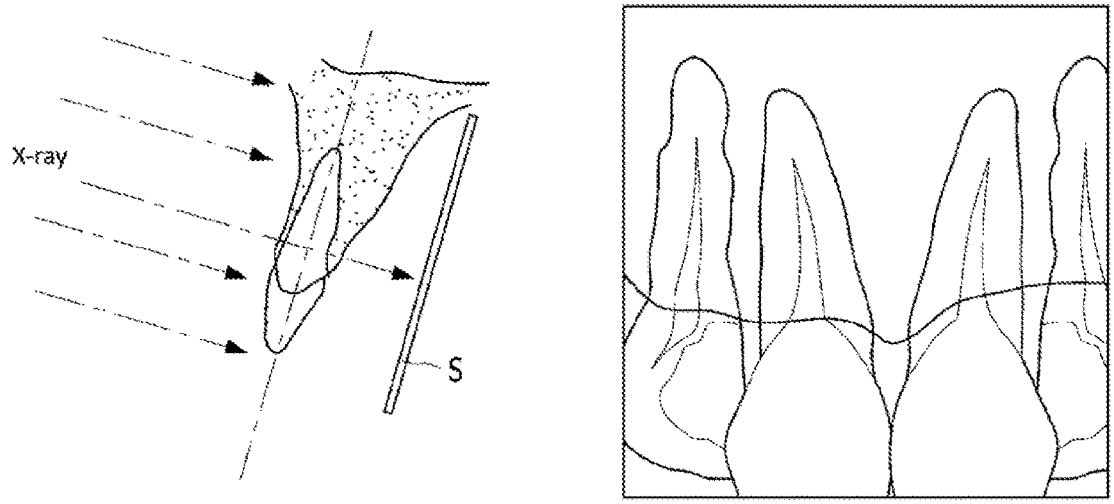
FIG. 1 shows principle of a general intra-oral X-ray radiography and an intra-oral X-ray image.
Figure 2:
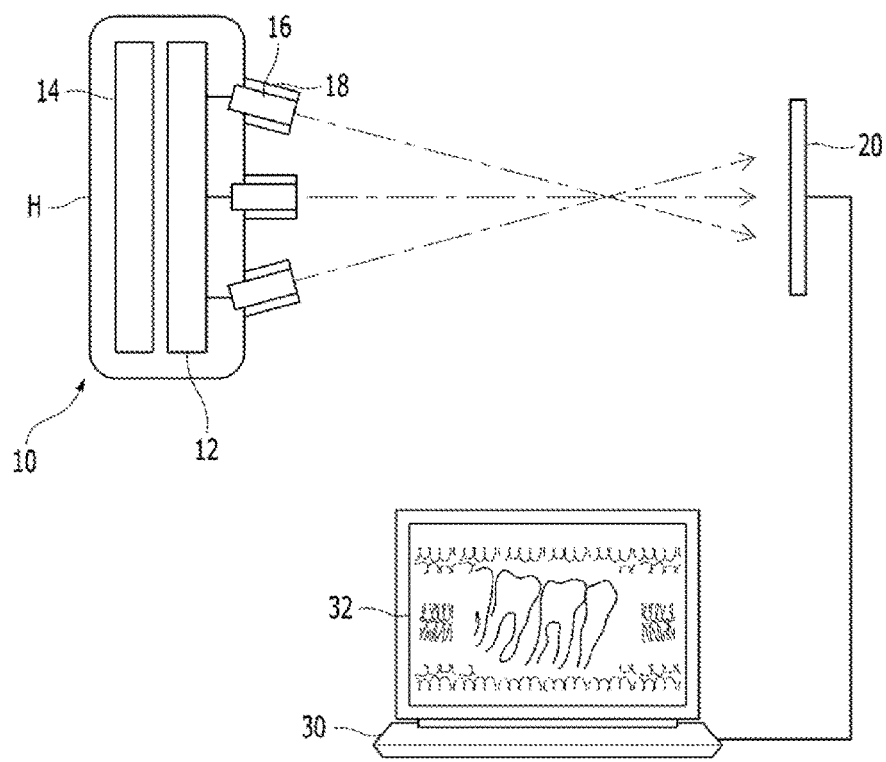
FIG. 2 shows a schematic configuration of an intra-oral X-ray imaging system according to the present invention.

FIG. 2 shows a schematic configuration of an intra-oral X-ray imaging system according to the present invention.

As shown in the drawing, an intra-oral X-ray imaging system according to the present invention includes: an X-ray generation apparatus 10 configured to irradiate X-rays to a tooth and surrounding tissue, namely a field of view inside a subject's mouth, from outside the mouth; an X-ray sensor apparatus 20 disposed inside the subject's mouth to face the X-ray generation apparatus with the field of view therebetween, and configured to detect the X-rays having penetrated through the field of view; and an image processing apparatus 30 configured to realize an X-ray image of the field of view based on X-rays projection data, namely a detection result of the X-ray sensor apparatus 20.

Here, particularly, the intra-oral X-ray imaging system according to the present invention is characterized in that: the X-ray generation apparatus 10 is configured to irradiate a plurality of X-rays to the field of view at the same angle or different angles; the X-ray sensor apparatus 20 is configured to detect the plurality of X-rays having penetrated through the field of view at the same angle or different angles; and the image processing apparatus 30 is configured to produce and display at least one X-ray image of a two-dimensional transmission image, a tomosynthesis image, and a three-dimensional CT image of the field of view, based on the plurality of X-rays projection data at the same angle or different angles, namely a detection result of the X-ray sensor apparatus 20.

In this case, preferably, the X-ray generation apparatus 10 irradiates the X-rays at the same angle or different angles at a rate of 1 to 20 frames per second, and the X-ray sensor apparatus 20 detects the X-rays at a rate of 1 to 20 frames per second.

Detailed description of main elements of the intra-oral X-ray imaging system according to the present invention is as follows.

The X-ray generation apparatus 10 includes: a plurality of X-ray sources 16 configured to respectively irradiate X-rays at the same angle or different angles to the X-ray sensor apparatus 20; a controller 12 configured to supply driving power and control signals for driving the X-ray sources 16; and a power supply 14 configured to supply driving power for the X-ray sources 16 and the controller 12, wherein the above elements of the X-ray generation apparatus are properly mounted in a body H.

Here, preferably, a side of the body H is provided with a plurality of cones 18, in which some or all of the plurality of X-ray sources 16 is mounted one-to-one, and the cones 18 serves to substantially adjust the direction of the X-rays of the X-ray sources 16.

Figure 3:
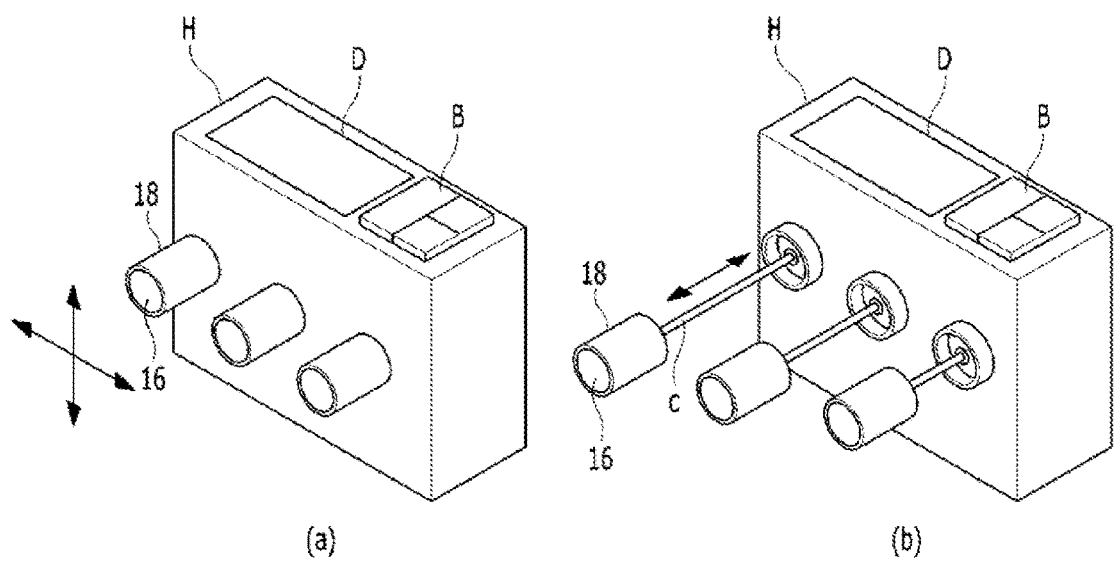
FIG. 3 shows an X-ray generation apparatus according to an embodiment of the present invention.

FIG. 3 shows an X-ray generation apparatus according to an embodiment of the present invention. See also FIG. 2.

As shown in the drawing, the controller 12 and the power supply 14 of the X-ray sensor apparatus 20 may be mounted in the body H, and a side of the body H, for example, a front surface thereof may be provided with the plurality of cones 18. Further, a side of the body H, for example, an upper surface thereof may be provided with a display device D and at least one button B as a user interface for inputting a user operation signal for driving and controlling the X-ray sources 16.

Further, some or all of the plurality of X-ray sources 16 is mounted one-to-one in the plurality of cones 18, wherein as shown in left view a, the plurality of cones 18 are connected to the body H by ball joints (not shown) and the angles may be individually adjusted. As another example, as shown in right view b, each of the cones 18 and the X-ray sources 16 may be detachable from the body H via a cable C connecting the X-ray sources 16 and the controller 12. Also in this case, it is possible to adjust the direction and angle of the X-rays irradiated by the respective X-ray sources 16 by adjusting the position and angle of the cones 18. For reference, the plurality of cones 18 may be provided with an adjusting means, such as a collimator, configured to adjust an irradiation range of the X-rays of the X-ray sources 16 mounted one-to-one in the cones. The power supply 14 may include a battery or a power cable connected to an external power source.

As a further example, the X-ray sources 16 may be modularized and detachably coupled to the body H as an X-ray source module. In this case, the X-ray sources may be coupled and separated through a coupling structure including a plurality of connection terminal electrodes such as a power terminal and a control signal terminal for power and control signal supply. The coupling structure may be mechanically configured such that an angle thereof is adjusted while the X-ray source module is mounted thereto.

As a result of this configuration, the X-ray generation apparatus 10 may individually drive the plurality of X-ray sources 16 using the power and the control signals of the power supply 14 and the controller 12 according to a user operation signal input to the at least one button B or control signals from the image processing apparatus, thereby irradiating a plurality of X-rays, and a plurality of X-rays at different angles may be irradiated toward the X-ray sensor apparatus 20 through the adjustment of the angle and position of the cones 18.

Figure 4:
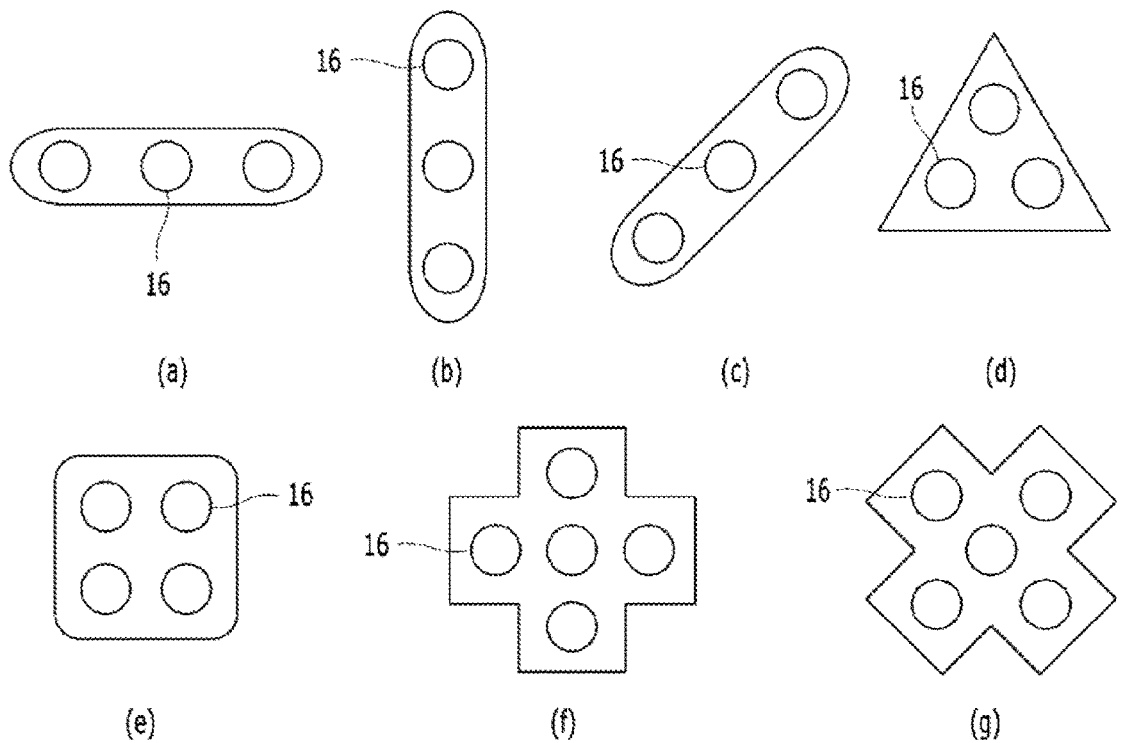
FIG. 4 shows an example of an arrangement of X-ray sources of the X-ray generation apparatus according to an embodiment of the present invention.

Meanwhile, although the three cones 18 and the X-ray sources 16 are disposed horizontally in FIG. 3, the positions and quantity of the cones 18 and the X-ray sources 16 may be freely adjusted according to the purpose. FIG. 4 shows an example of an arrangement of the X-ray sources of the X-ray generation apparatus according to an embodiment of the present invention. The cones are omitted for convenience.

As shown in the drawings, the three X-ray sources 16 of the X-ray generation apparatus may be arranged horizontally (FIG. 4a), vertically (FIG. 4b), diagonally (FIG. 4c), or triangularly (FIG. 4d). Alternatively, the four X-ray sources 16 may be arranged in a quadrangular shape (FIG. 4e), a cruciform intersecting vertically and horizontally (FIG. 4f), or an X-shape crossing in the left and right diagonal (FIG. 4g). However, these are only a few examples, and the positions and quantity of the X-ray sources 16 may be variously modified according to the purpose.

Meanwhile, preferably, the plurality of X-ray sources 16 provided in the X-ray generation apparatus 10 are electric field emission type X-ray sources using a nanostructure emitter, such as a CNT (carbon nanotube). As is well known, an electric field emission type X-ray source apparatus can obtain high-efficiency X-rays with low power, pulse drive is possible since an operation period is short, and it is small size and light weight. Accordingly, it is suitable for the X-ray generation apparatus 10 of the present invention, in which the plurality of X-ray sources 16 are provided in a single apparatus and individually driven. Further, in this case, the X-ray generation apparatus 10 is capable of irradiating X-rays at a rate of 1 to 20 frames per second.

Figure 5:
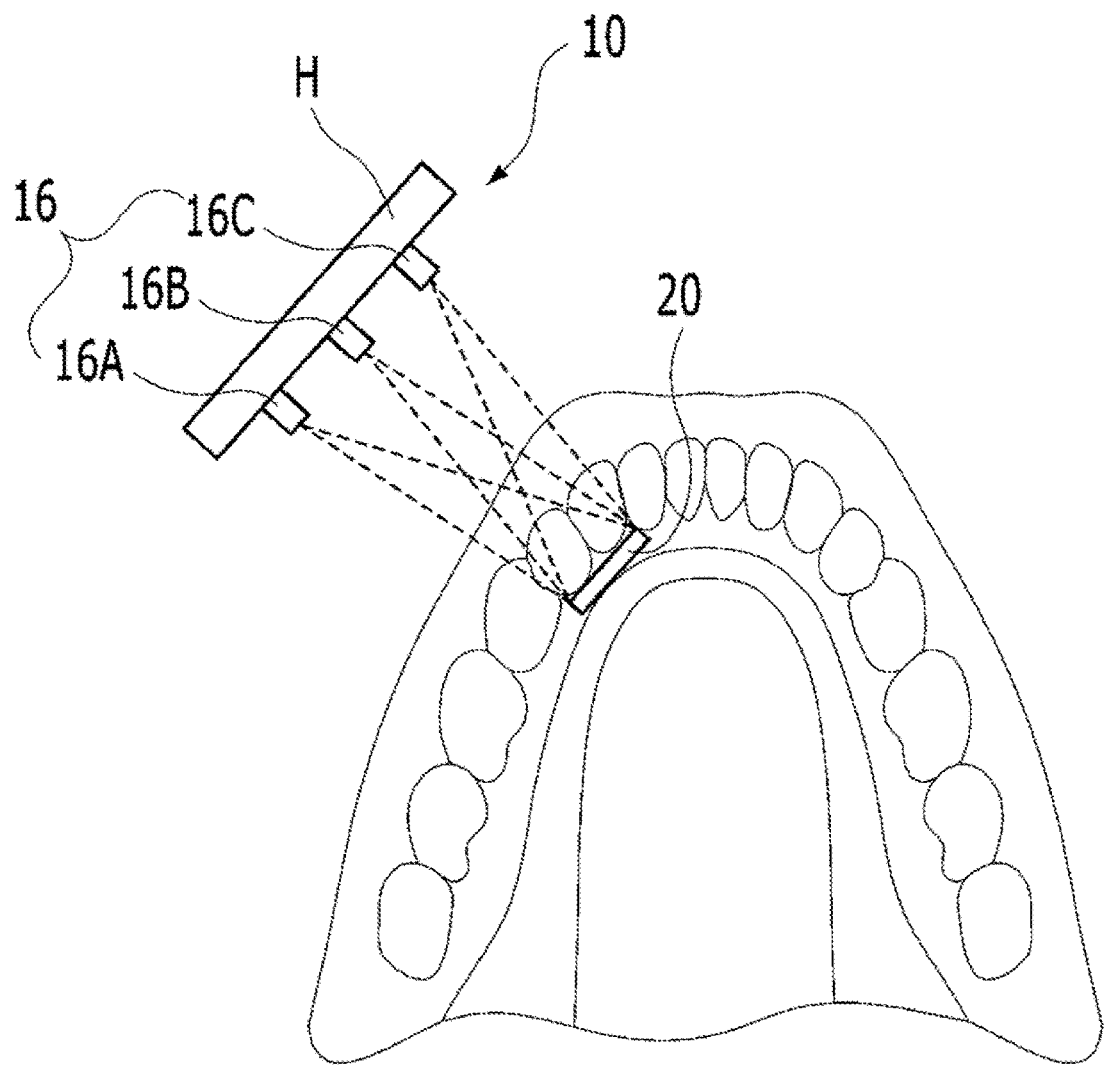
FIG. 5 shows performing radiography using the X-ray generation apparatus according to an embodiment of the present invention.

FIG. 5 shows performing radiography using the X-ray generation apparatus according to an embodiment of the present invention.

As described above, particularly, the X-ray generation apparatus 10 of the intra-oral X-ray imaging system according to the present invention is configured such that the plurality of X-ray sources 16 irradiates X-rays at a same angle or different angles to the field of view, more specifically, to the X-ray sensor apparatus 20 disposed to face the X-ray generation apparatus with the field of view therebetween, on a frame-by-frame basis, and the X-ray sensor apparatus 20 detects the X-rays having penetrated through the field of view at the same angle or different angles on a frame-by-frame basis. As shown in the drawing, in the case of providing three X-ray sources 16A, 16B, and 16C, the left X-ray source 16A irradiates X-rays that can form a one-frame transmission image, to the X-ray sensor apparatus 20 disposed behind the field of view for a predetermined time. Here, the X-ray sensor apparatus 20 transmits projection data A of the frame to the image processing apparatus. Then, the middle X-ray source 16B irradiates X-rays again that can form a one-frame transmission image. The X-ray sensor apparatus 20 transmits projection data B of the frame to the image processing apparatus, and this process is repeated for the right X-ray source 16C to acquire projection data C.

Meanwhile, preferably, the X-ray sensor apparatus may transmit X-ray projection data to the image processing apparatus at a rate of 1 to 20 frames per second, whereby the image processing apparatus may display a real-time X-ray video clip.

Referring back to FIG. 2, the image processing apparatus 30 of the intra-oral X-ray imaging system according to the present invention is configured to construct an image expressed in gray scale by using an X-ray detection result transmitted on a frame-by-frame basis from the X-ray sensor apparatus 20, and produce and display at least one of a two-dimensional transmission image, a tomosynthesis image, and a three-dimensional CT image of the field of view. To achieve this, the image processing apparatus 30 may include a monitor 32 configured to display the X-ray image. Meanwhile, the X-ray detection result of the X-ray sensor apparatus 20 may be transmitted to the image processing apparatus 30 by wire or wirelessly.

When the image processing apparatus 30 displays a transmission image, a two-dimensional X-ray projection data acquired by irradiating X-rays at the same angle or different angles, that is, one of the projection data A, B, and C may be displayed as a two-dimensional transmission image of the field of view. In some cases, a two-dimensional transmission image that is constructed by superimposing the projection data A, B, and C in a plane may be displayed.

When the image processing apparatus 30 displays a tomosynthesis image, a tomosynthesis image may be constructed through a publicly known three-dimensional tomosynthesis image algorithm by using two-dimensional projection data at different angles from each other, that is, the projection data A, B, and C. For example, it is possible to display a three-dimensional tomosynthesis image of a field of view by reconstructing data through SAA (Shift And ADD) algorithm that obtains a tomographic image by back-projecting each of the two-dimensional projection data to a plane of interest (POI). A user can identify a conventional intra-oral X-ray image or the three-dimensional tomosynthesis image reflecting the depth information on an arbitrary point depending on the purpose. When the image processing apparatus 30 displays a CT image, a three-dimensional image may be provided by reconstructing the plurality of projection data acquired on a frame-by-frame basis through reconstruction algorithm. However, to construct a CT image, projection data acquired from more diverse angles than the tomosynthesis image may be required.

Figure 6:
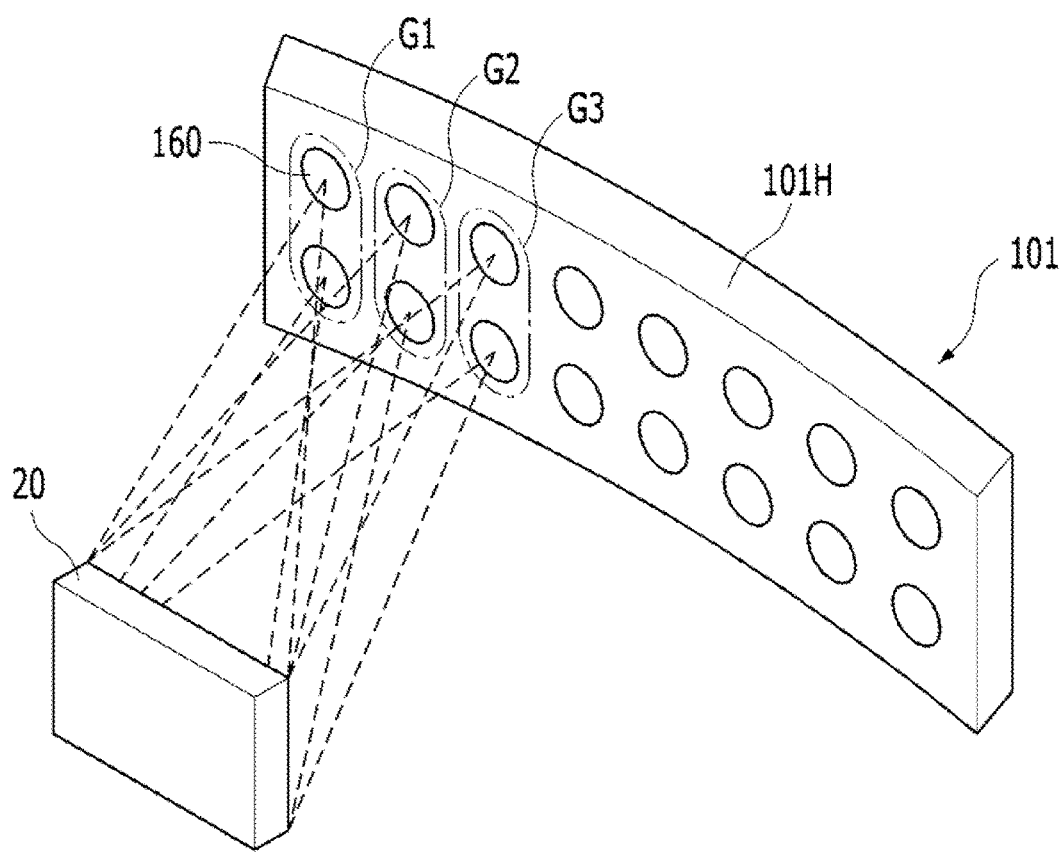
FIG. 6 shows an X-ray generation apparatus according to an embodiment of the present invention.

FIG. 6 shows an X-ray generation apparatus according to an embodiment of the present invention.

In the X-ray generation apparatus 101 according to the embodiment of the present invention, the plurality of X-ray sources is arranged in an array on a single body 101H, and includes a plurality of X-ray source elements 160 using an electric field emission type nanostructure emitter. Each of the plurality of X-ray sources is constituted by X-ray source element groups G1, G2, and G3 each including at least one X-ray source element 160. The plurality of X-ray source element groups G1, G2, and G3 may be driven in groups. In other words, a controller provided in the body 101H of the X-ray generation apparatus 101 according to the embodiment of the present invention may drive the plurality of X-ray source elements 160 arranged in an array, individually or in groups. In this case, the driven X-ray source element groups G1, G2, and G3 irradiate X-rays to the X-ray sensor apparatus 20 in the same direction or different directions, to respectively form a one-frame X-ray transmission image.

Meanwhile, in the drawing, for example, when a plurality of X-rays projection data is acquired through driving from an X-ray source element group G1 disposed on the left side of the body 101H to an X-ray source element group on the right side thereof, an X-ray CT image may be reconstructed in the image processing apparatus by using the projection data. In this case, the plurality of X-ray source elements 160 and the X-ray sensor apparatus 20 constitutes a Multi-Source Inverse-Geometry CT system having a plurality of scattered focal spots, whereby it is possible to reconstruct a three-dimensional CT image of the field of view (FOV) that is larger than the sensor area of the X-ray sensor apparatus 20. As a result of this configuration, it is possible to provide a CT image of a sufficient area of a field of view for dental diagnosis while alleviating the sensation of a foreign body by inserting the small-sized X-ray sensor apparatus 20 into a subject's mouth.

Figure 7:
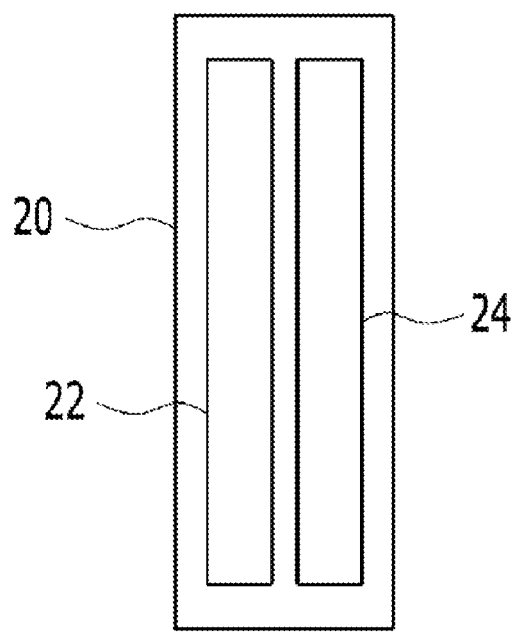
FIG. 7 schematically shows a cross section of an X-ray sensor apparatus according to an embodiment of the present invention.

FIG. 7 schematically shows a cross section of an X-ray sensor apparatus according to an embodiment of the present invention.

As shown in the drawing, the X-ray sensor apparatus 20 includes: an X-ray sensor 22 configured to detect X-rays; and a readout circuit 24 configured to read out a detection result of the x-ray sensor 22 to the image processing apparatus 30. Here, the X-ray sensor apparatus 20 reads out the X-ray detection result of the x-ray sensor 22 on a frame-by-frame basis. Further, the readout circuit 24 may divide the X-ray sensor 22 into a plurality of sections, and may read out the X-ray detection result on a multi-channel basis through a separate channel for each section.

Figure 8:
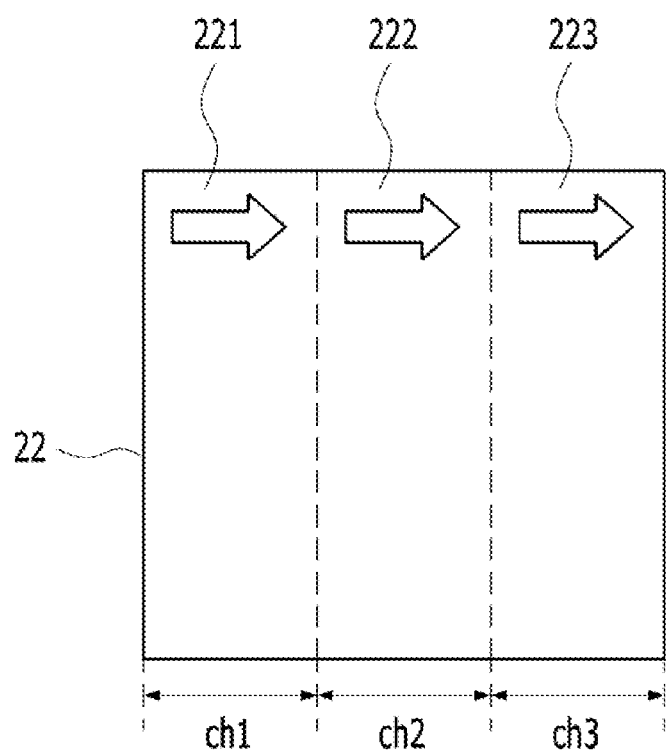
FIG. 8 schematically shows the concept of a multi-channel readout of the X-ray sensor apparatus according to an embodiment of the present invention.

FIG. 8 schematically shows the concept of a multi-channel readout of the X-ray sensor apparatus according to an embodiment of the present invention.

The readout circuit 24 may divide an incident surface of the X-ray sensor 22 into at least two sections, and allocate an individual readout channel to each section, thereby simultaneously reading out each channel. The embodiment is configured such that the incident surface of the X-ray sensor 22 is divided into three sections 221, 222, and 223, and three separate readout channels ch1, ch2, and ch3 are respectively allocated to each section, thereby simultaneously reading out each channel. As a result, the X-ray sensor apparatus 20 shortens the readout time of one frame by one third, thereby detecting and reading out X-rays irradiated on a frame-by-frame basis from the at least two X-ray sources, at high speed.

For reference, although not shown in the drawing, it is also possible that two or more X-ray sensors 22 or X-ray sensor apparatuses 20 are arranged along a back and forth direction with respect to the x-ray generation apparatus, wherein a predetermined filter may be disposed between the two different X-ray sensors 22 or X-ray sensor apparatuses 20. In this case, in each of the X-ray sensors 22 or the X-ray sensor apparatuses 20, X-ray detection results of different energy levels which are gradually decreased by the filter may be obtained, and depending on the energy levels, X-ray images optimized for soft tissues such as skin and x-ray images optimized for hard tissues such as teeth may be obtained, which will be easily understood by those skilled in the art even though there are no separate drawings.

Further, if necessary, the X-ray sensor apparatus 20 may be a so-called flexible sensor or a bendable sensor that is bent within a predetermined range according to the shape of a tooth and surrounding tissues in the mouth, whereby it is possible to alleviate the pain that a patient may experience during the X-ray radiography process.

Figure 9:
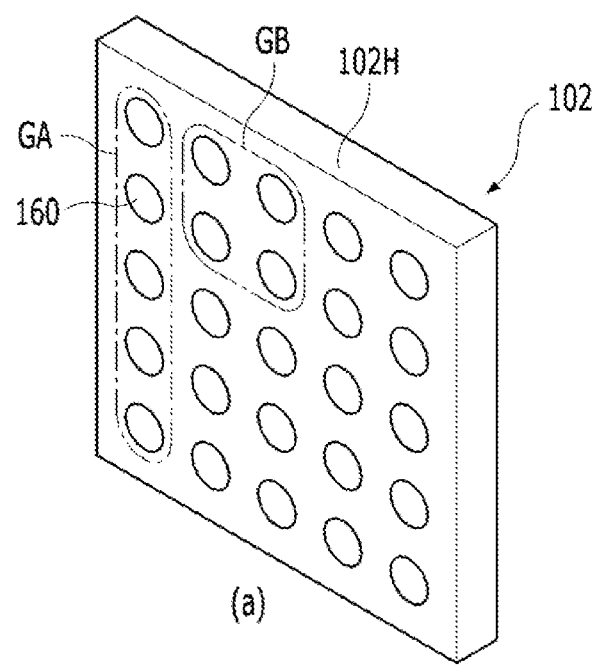
FIG. 9 shows X-ray generation apparatuses according to various embodiments of the present invention.
Figure 9:
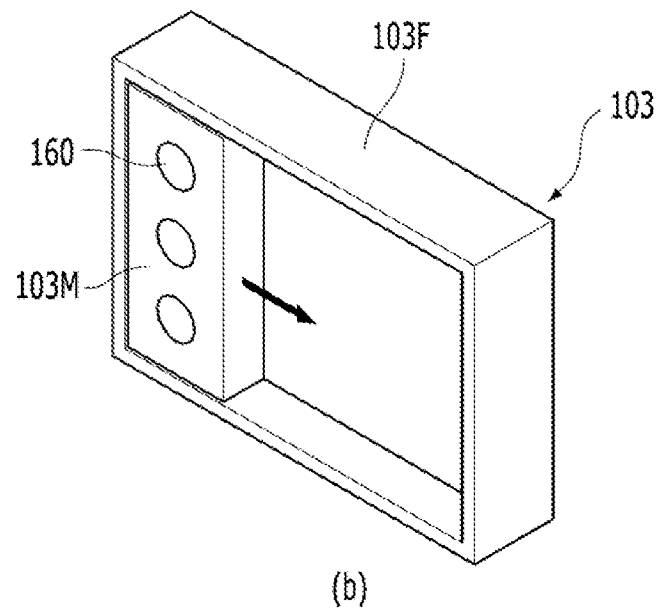

FIG. 9 shows X-ray generation apparatuses according to various embodiments of the present invention. As shown in the drawings, upper view a shows an example of an X-ray generation apparatus 102 including a plurality of X-ray source elements 160 arranged in a quadrangular array on the body 102H; and lower view b shows an example of an X-ray generation apparatus 103 further including a guide frame 103F configured to guide a single body 103M to move within a predetermined range.

Firstly, looking at the X-ray generation apparatus 102 of view a, a plurality of X-ray source elements 160, for example, twenty five X-ray source elements 160 are arranged in a 5×5 matrix. These are grouped into one or more than one to form X-ray source element groups GA and GB, wherein a vertically long group, like the left X-ray source element group GA, may be formed, or a square-shaped group, like the upper X-ray source element group GB, may be formed. The array form of the X-ray source element groups is not limited to these, and may be variously grouped. Further, the X-ray source element groups are not fixed, but may be set to vary according to the position and size of the field of view.

Next, looking at the X-ray generation apparatus 103 of view b, a plurality of X-ray source elements 160 are arranged vertically in a single body 103M, and during a series of X-ray radiography processes, the body 103M itself moves along the guide frame 103F to irradiate X-rays at various angles. Herein, the plurality of X-ray source elements 160 may be individually driven or may be driven in groups by grouping two or more source elements in a group. Here, preferably, apart from movement of the body 103M, the plurality of X-ray source elements 160 are configured to irradiate X-rays at various angles while moving with respect to the body 103M, and to achieve this, an additional guide frame is provided in the body 103M to allow the plurality of X-ray source elements 160 to be moved.

Figure 10:
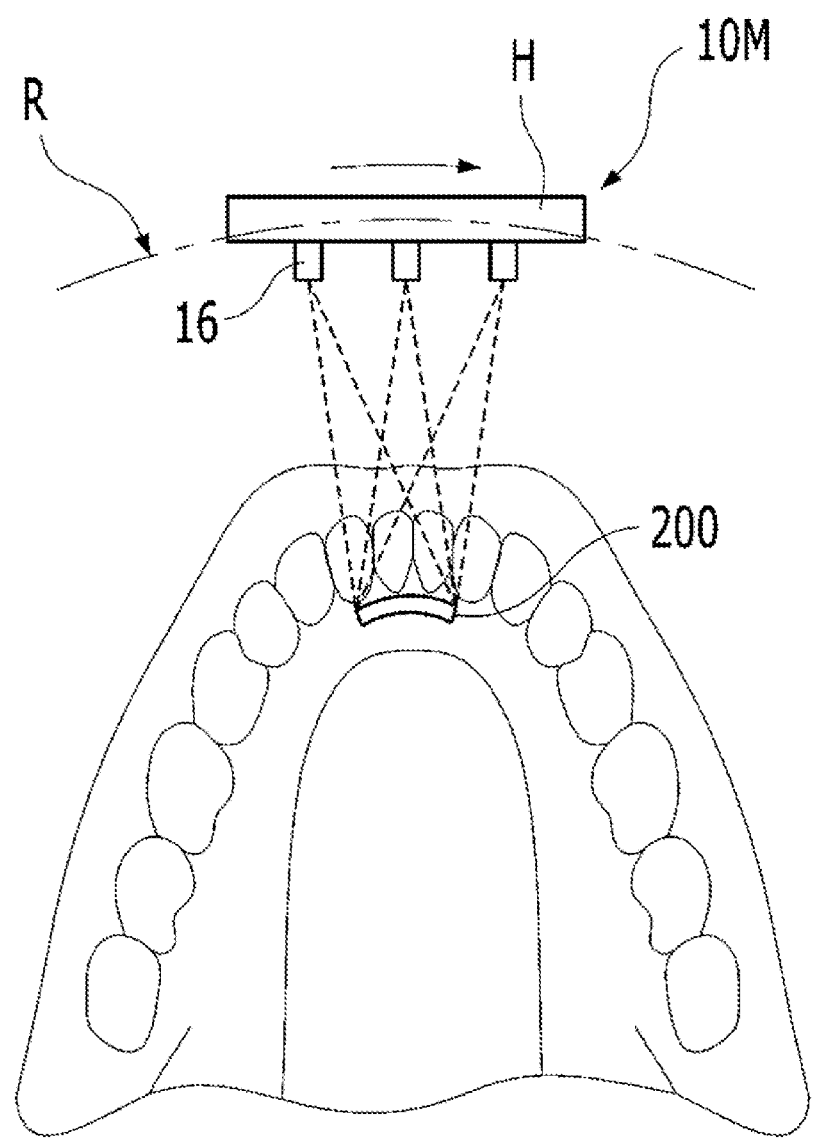
FIG. 10 shows performing radiography using an X-ray generation apparatus according to an embodiment of the present invention.

FIG. 10 shows performing radiography using an X-ray generation apparatus according to an embodiment of the present invention.

As shown in the drawing, an X-ray generation apparatus 10M according to the embodiment of FIG. 10 and an intra-oral X-ray imaging system including the same are common to the embodiment shown in FIG. 2 or 5 in that it has a plurality of X-ray sources 16 arranged at various positions on one body H of the X-ray generation apparatus 10M, but the X-ray generation apparatus 10M according to the embodiment of the present invention is different from the embodiment shown in FIG. 2 or 5 in that it is configured to move along a predetermined trajectory R during a series of X-ray radiography processes. Herein, the predetermined trajectory R may be, for example, an arc-shaped trajectory, but is not limited thereto. The predetermined trajectory R may be substantially realized by rails or various types of guide frames that guide the path of the body H.

The X-ray generation apparatus 10M according to the embodiment of the present invention and the intra-oral X-ray imaging system are configured to move plurality of X-ray sources 16 and/or the body H in parallel with driving a plurality of X-ray sources 16 while driving the plurality of X-ray sources 16, whereby it is possible to obtain X-rays projection data of more frames imaged at more varying angles during a series of intra-oral X-ray radiographies. Accordingly, it is possible to provide a high-quality X-ray CT image with a small-sized intraoral x-ray sensor apparatus 200.

Meanwhile, herein, the X-ray sensor apparatus 200 may include a so-called flexible sensor or a bendable sensor that is bent within a predetermined range according to the shape of a tooth and surrounding tissues in the mouth, or may include a curved X-ray sensor curved at a predetermined curvature. In the case of the curved X-ray sensor, it may be variously provided with various curvatures depending on the position where the X-ray sensor apparatus 200 is mainly disposed in the mouth. Thereby, it is possible to alleviate the pain that a patient may experience during the X-ray radiography process.

Figure 11:
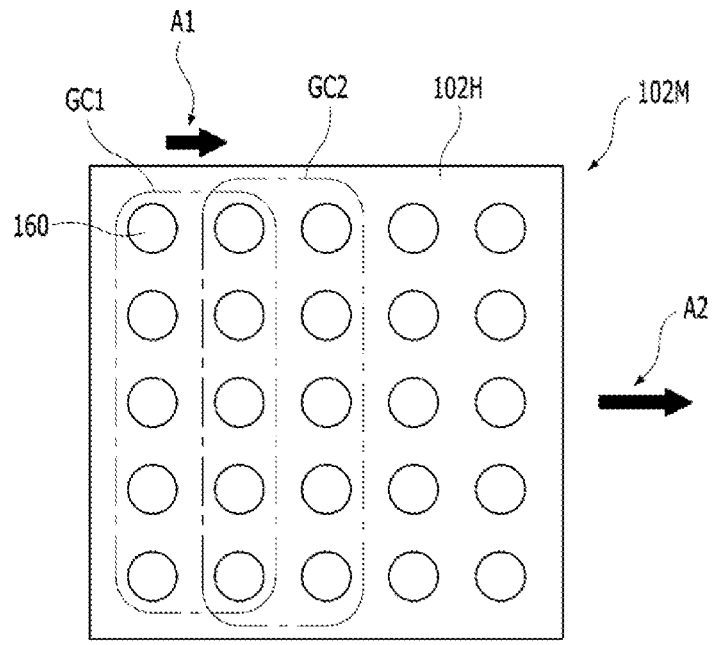
FIG. 11 shows an X-ray generation apparatus according to an embodiment of the present invention.

FIG. 11 shows an X-ray generation apparatus according to an embodiment of the present invention.

An X-ray generation apparatus 102M according to the embodiment of the present invention is similar to the apparatus according to the embodiment shown in FIG. 7a, but is different therefrom in that a body 102H of the X-ray generation apparatus 102M is configured to be movable along a predetermined trajectory. As an example, in the case of a series of X-ray radiography processes, X-ray projection data of a frame corresponding to each group GC1, GC2 is acquired in the X-ray sensor apparatus while driving X-ray source element groups GC1 and GC2, each of which is constituted by one or a plurality of X-ray source elements 160, in a direction of arrow A1, and at the same time, it is possible to move the body 102H in a direction of arrow A2. The driving of the X-ray source element groups GC1 and GC2 and the movement of the body 102H may be performed at the same time, and the driving of the entire group and the movement of the body 102H may be repeatedly performed alternately.

Meanwhile, the plurality of X-ray source element groups GC1 and GC2 may be grouped such that each group shares some of the X-ray source elements 160. It is preferred that a plurality of X-ray source element groups is configured such that the X-ray irradiation range of one group covers at least an area of a corresponding X-ray sensor. Further, although not shown in the drawing, a collimator may be provided in the path of X-rays of the X-ray generation apparatus, which is configured to adjust the irradiation range of the X-rays that are irradiated by driving each group such to cover an area of the X-ray sensor, respectively.

Figure 12:
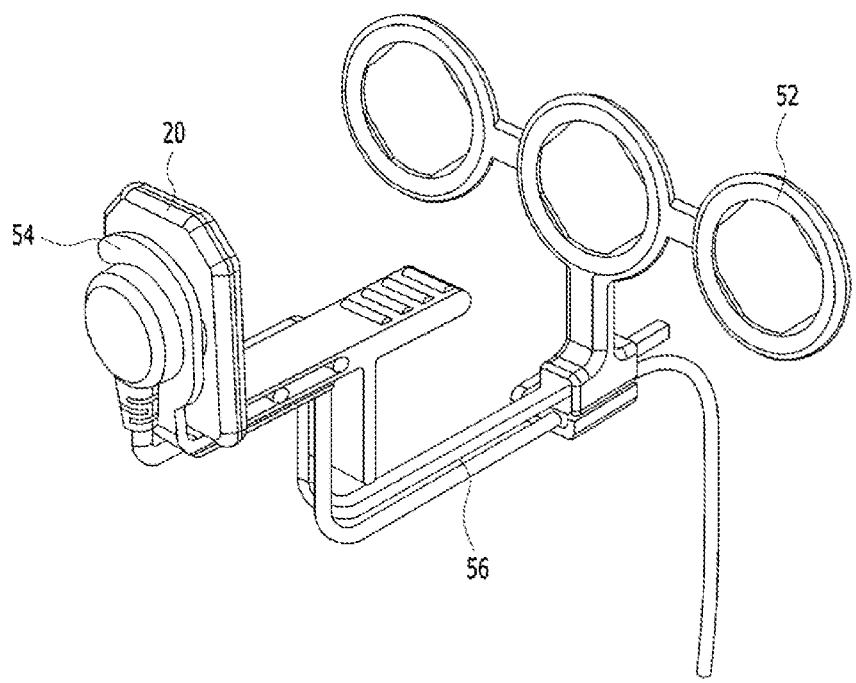
FIG. 12 shows an example of a guide holder for intra-oral X-ray radiography.

FIG. 12 shows an example of a guide holder for intra-oral X-ray radiography.

As shown in the drawing, a guide holder applied to an intra-oral X-ray imaging system according to an embodiment of the present invention includes: at least two source fasteners 52 configured to allow at least two X-ray sources to be fastened one-to-one thereto; a sensor fastener 54 configured to fasten an X-ray sensor apparatus 20; and a loader 56 configured to connect the at least two source fasteners 52 and the sensor fastener 54 to face each other with a predetermined interval.

Here, the at least two source fasteners 52 may exhibit an arrangement relation, in which an optimal two-dimensional transmission image and a three-dimensional tomosynthesis image can be obtained, in consideration of the distance between the source fasteners or the distance to the sensor fastener 54. As a result, the cones 18 of the X-ray generation apparatus 10 shown in FIG. 3 are respectively inserted into each of the at least two source fasteners 52 such that the positions and angles thereof are fixed, and on the other hand, when he X-ray sensor apparatus 20 is fastened to the sensor fastener 54, the at least two X-ray sources 16 and the X-ray sensor apparatus 20 have the optimal arrangement relation, in which a two-dimensional transmission image and a three-dimensional tomosynthesis image may be obtained according to the purpose. Accordingly, with the arrangement relation maintained, the sensor fastener 54 and the X-ray sensor apparatus 20 are aligned at desired positions in the subject's mouth, and then X-rays on a frame-by-frame basis are sequentially irradiated from the at least two X-ray sources 16, whereby it is possible to obtain an accurate two-dimensional transmission image and a three-dimensional tomosynthesis image of the field of view at all times.

For reference, it is obvious to those skilled in the art that the detailed shape of the guide holder according to the present invention, such as the loader 56, can be variously modified according to the purpose of radiography or the position of the field of view, for example, anterior tooth, canine, posterior tooth, abutment tooth, or the like, and as in the above description, the position and quantity of the source fastener 52 may be variously modified according to the positions and quantity of the cones 18 and the X-ray sources 16 of the X-ray generation apparatus 10.

As described above, although reference to the embodiments has allowed the present invention to be described in more detail, it should be understood that the present invention is not limited to the embodiments but may be variously changed without departing from the technical idea of the present invention. Therefore, the embodiments disclosed in the present invention are not restrictive but are illustrative, and the scope of the technical idea of the present invention is not limited to the embodiments. The scope of the present invention should be interpreted by the accompanying claims, and it is to be understood that all technical ideas within the claims fall within the purview of the present invention.

INDUSTRIAL APPLICABILITY

The present invention may be used in dental or medical X-ray diagnostic equipment as well as industrial non-destructive testing equipment.

The invention claimed is:

1. An X-ray generation apparatus for intra-oral X-ray imaging irradiating X-rays to a field of view, the X-ray generation apparatus comprising:
   a body; and
   a plurality of X-ray sources disposed in different positions of the body, and configured to irradiate X-rays to the field of view,
   wherein the body moves along a predetermined trajectory for the field of view, and
   wherein each of the X-ray sources includes an X-ray source module, and the X-ray source module is detachably coupled to the body.

2. The X-ray generation apparatus of claim 1, wherein each of the plurality of X-ray sources irradiates X-rays to form a unit frame of X-ray image for the field of view.

3. The X-ray generation apparatus of claim 1, further comprising:
   a controller provided in the body, and configured to supply power and control signals for driving the plurality of X-ray sources.

4. The X-ray generation apparatus of claim 3, wherein the body moves along a predetermined trajectory for the field of view, and
   the controller drives the plurality of X-ray sources in conjunction with the movement of the body.

5. The X-ray generation apparatus of claim 3, wherein the controller drives the plurality of X-ray sources in conjunction with movement of the plurality of X-ray sources.

6. The X-ray generation apparatus of claim 1, wherein the X-ray source module adopts an electric field emission type nanostructure emitter.

7. The X-ray generation apparatus of claim 1, wherein the plurality of X-ray sources is arranged on the body, and includes a plurality of X-ray source elements adopting an electric field emission type nanostructure emitter, wherein each of the X-ray sources includes at least one X-ray source element.

8. The X-ray generation apparatus of claim 2, wherein the plurality of X-ray sources irradiates the X-rays at a rate of 1 to 20 frames per second.

9. The X-ray generation apparatus of claim 1, further comprising: a guide holder comprising:
   at least two source fasteners disposed outside a subject's mouth, and configured to fasten at least two X-ray sources respectively irradiating X-rays;
   a sensor fastener disposed inside the subject's mouth, and configured to fasten an X-ray sensor apparatus that detects the X-rays irradiated from the respective X-ray sources; and
   a loader configured to connect the source fasteners and the sensor fastener.

10. The guide holder of claim 9, wherein the sensor fastener is configured to allow two or more X-ray sensor apparatuses disposed in a back and forth direction with respect to the source fastener to be fastened thereto.

11. An X-ray generation apparatus for intra-oral X-ray imaging irradiating X-rays to a field of view, the X-ray generation apparatus comprising:
   a body configured to move along a predetermined trajectory for the field of view;
   a plurality of X-ray sources disposed in different positions of the body, and configured to irradiate X-rays to the field of view; and
   a guide holder comprising:
      at least two source fasteners disposed outside a subject's mouth, and configured to fasten at least two X-ray sources respectively irradiating X-rays;
      a sensor fastener disposed inside the subject's mouth, and configured to fasten an X-ray sensor apparatus that detects the X-rays irradiated from the respective X-ray sources; and
      a loader configured to connect the source fasteners and the sensor fastener.

* * * * *